United States Patent [19]

Wyvratt

[11] Patent Number: 4,500,736
[45] Date of Patent: Feb. 19, 1985

[54] HYDROGENATION OF 3-TRICHLOROVINYLNITROBENZENE

[75] Inventor: Jean M. Wyvratt, Mountainside, N.J.

[73] Assignee: Merck & Co., Inc., Rahway, N.J.

[21] Appl. No.: 508,063

[22] Filed: Jun. 28, 1983

Related U.S. Application Data

[63] Continuation-in-part of Ser. No. 414,116, Sep. 2, 1982, abandoned.

[51] Int. Cl.$^3$ .............................................. C07C 85/11
[52] U.S. Cl. ..................................................... 564/417
[58] Field of Search ........................................ 564/417

[56] References Cited

U.S. PATENT DOCUMENTS

| | | | |
|---|---|---|---|
| 2,884,458 | 4/1959 | Fidler | 564/417 |
| 3,051,753 | 8/1962 | Dietzler | 260/580 |
| 3,067,253 | 12/1962 | Dietzler et al. | 564/417 |
| 3,073,865 | 1/1963 | Spiegler | 260/580 |
| 3,868,403 | 2/1975 | Becker et al. | 564/417 X |
| 3,989,756 | 11/1976 | Fujise et al. | 564/417 |
| 4,020,107 | 4/1977 | Kosak | 564/417 |
| 4,059,627 | 11/1977 | Kritzler et al. | 564/417 X |
| 4,064,239 | 12/1977 | Mrozik | 424/228 |

OTHER PUBLICATIONS

*Catalytic Hydrogenation*, Robert L. Augustine, pp. 126–127, Mercel Dekker Inc. Publisher (1965).
*Catalytic Hydrogen in Organic Synthesis*, Paul N. Ryland, pp. 124 to 126, Academic Press publishers (1979).
*Journal of American Chemical Society*, Dovell et al., 87, pp. 2767 to 2768 (1965).
*Journal of American Chemical Society*, Baltzly et al., 68, pp. 261 to 265 (1946).
Seagraves, *Chemical Abstracts*, 93, 93:94965p (1980).

*Primary Examiner*—Paul F. Shaver
*Attorney, Agent, or Firm*—David L. Rose; Hesna J. Pfeiffer

[57] ABSTRACT

There is disclosed a process for the conversion of 3-trichlorovinylnitrobenzene to 3-trichlorovinylaniline by catalytic reduction in an alcoholic acidic medium, using a supported palladium catalyst in a hydrogen atmosphere. The process is carried out without any appreciable hydrogenolysis of the trichlorovinyl group.

9 Claims, No Drawings

4,500,736

HYDROGENATION OF 3-TRICHLOROVINYLNITROBENZENE

CROSS REFERENCE TO RELATED APPLICATIONS

This application is a continuation-in-part of my co-pending application Ser. No. 414,116, filed Sept. 2, 1982, now abandoned.

BACKGROUND OF THE INVENTION

The compound 3-trichlorovinylaniline is an intermediate for the preparation of 4-amino-6-trichlorovinyl-1,3-benzenedisulfonamide which is a compound highly effective in the treatment of fasciola (liver fluke) infections in animals. The compound is disclosed in U.S. Pat. No. 4,064,239 to Mrozik issued Dec. 20, 1977. In such reference, the reduction of the nitro group is discussed using such reagents as iron in hydrochloric acid or zinc in acetic acid. It is known that the use of such stronger reducing agents as hydrogen and supported palladium cannot be used in the presence of the trichlorovinyl group since such group will be subject to hydrogenolysis (see Augustine Catalytic Hydrogenation pp. 126–127, Marcel Dekker, Inc.—Publisher (1965)). However, it has been unexpectedly discovered that using certain reaction conditions discussed below, the hydrogenolysis of the trichlorovinyl group is avoided and the yields of the 3-trichlorovinylaniline are improved.

SUMMARY OF THE INVENTION

This invention is concerned with an improved hydrogenation process for the preparation of 3-trichlorovinylaniline and acid addition salts thereof such as the hydrochloride salt. Thus it is an object of the instant application to describe the hydrogenation process and catalyst therefore. A further object is to describe the specific reaction conditions which produce the unexpected increase in yields and unexpected decrease in hydrogenolysis of the trichlorovinyl side chain. Further objects will become apparent from a reading of the following description.

DESCRIPTION OF THE INVENTION

The instant invention is concerned with an improved process for the preparation of 3-trichlorovinylaniline from 3-trichlorovinylnitrobenzene. The process is carried out in an atmosphere of hydrogen at from 1 to 7 atmospheres of pressure (15–105 psig), preferably about 30–50 psig pressure is employed at the initiation of the reaction. Most preferably about 40 psig is employed. The catalyst employed is finely powdered palladium. The palladium is preferably supported on a substrate such as carbon and is present on the substrate at a rate of about 5 to 10% by weight. The thus supported catalyst is present in the reaction mixture at a rate of about 0.2 to 2.0% by weight of the 3-trichlorovinylnitrobenzene.

The hydrogenolysis of the trichlorovinyl group has been prevented in the instant reaction by carrying out the reaction in an alcoholic acidic medium which is preferably methanol or ethanol containing dissolved anhydrous hydrogen chloride or methanol or ethanol mixed with concentrated aqueous hydrochloric acid. The acid is present to such an extent as to maintain the reaction mixture at a pH of about 2.

The solvent may also contain additional solvents such as benzene or toluene or methylene chloride. Other acids may be used in the reaction such as sulfuric acid, however, hydrochloric acid is preferred.

The reaction is carried out at about room temperature although temperatures of from 0° to 50° C. may also be employed. The reaction is complete when the calculated stoichiometric amount of hydrogen has been absorbed. This is generally observed by following the drop in pressure in the hydrogenation apparatus as the reaction proceeds. This will vary depending on the temperature, specific activity level of the catalyst and the like. However, generally, the reaction is complete in from about 5 to 40 hours. The product is recovered using techniques known to those skilled in the art and is converted to the final product 4-amino-6-trichlorovinyl-1,3-benzenedisulfonamide using the procedures described in the above U.S. Pat. No. 4,064,239.

When 3-trichlorovinylaniline is prepared using the process of the instant invention, yields in excess of 90% can be expected. When 3-trichlorovinylaniline is prepared in the absence of the acidic medium employed in the instant invention, yields of up to only about 82% are realized owing to the hydrogenolysis of the trichlorovinyl side chain. The prior art processes are capable of producing the 3-trichlorovinylaniline in yields of up to about 90%. In doing so however, the 3-trichlorovinylaniline prepared using such known reduction techniques produces a residue of a metallic sludge which is difficult to properly dispose of. In such reactions, the quantity of metal (iron or zinc) is generally of the same weight as the product being reduced, thus, considerable sludge is produced during the course of the reaction. The instant process affords no such sludge.

The 3-trichlorovinylnitrobenzene starting material is prepared using known procedures. One such procedure starts with trichloromethyl-3-nitrobenzyl alcohol and phosphorous pentachloride to prepare 3-nitrotetrachloroethylbenzene. This is treated with base to prepare the 3-trichlorovinylnitrobenzene.

The following examples are supplied in order to more fully explain the process of the instant invention. They are not to be construed as limitative of the invention.

EXAMPLE 1

3-Nitrotetrachloroethylbenzene

To a 1-liter, 3-neck flask equipped with a mechanical stirrer, a thermometer, a 250-ml dropping funnel with pressure equalizing side-arm and a nitrogen inlet was charged 92.9 grams (0.446 mol) of phosphorous pentachloride and 300 ml of methylene chloride. A solution of 100 grams (0.37 mol) of trichloromethyl-3-nitrobenzyl alcohol in 180 ml of methylene chloride (heating was necessary for complete dissolution) was added dropwise over a 1 hour period to the above slurry. The temperature of the reaction rose from 23° C. to 33° C. during the addition. The temperature can be controlled by the rate of addition and no problems were encountered when the reflux temperature of methylene chloride was reached. Hydrogen chloride was evolved during the addition and all of the suspended solid dissolved to afford a clear, light yellow solution.

The reaction was complete as determined by gas chromatographic analysis after the addition of the trichloromethyl-3-nitrobenzyl alcohol, but the reaction mixture was stirred for an additional 3.5 hours at ambient temperature prior to quenching. Then it was added to 500 ml of ice-water with vigorous stirring. A temperature increase was observed upon quenching so external cooling at this point is recommended. The two-phase mixture was stirred for an additional hour at ambient temperature after the addition to the ice-water was completed. The layers were separated and the aqueous layer was extracted with 100 ml of additional methylene chloride. The combined organic layers were washed with 300 ml of water to which 25 ml of saturated aqueous sodium chloride solution had been added and then with 300 ml of 5% sodium hydroxide solution to which 25 ml of saturated sodium chloride solution had been added.

The two aqueous wash solutions were extracted with 50 ml of methylene chloride. The combined organic layers were washed with 300 ml of water and concentrated in vacuo to 107.83 gm of crude 3-nitrotetrachloroethylbenzene as a gold oil. This material was used directly in the next reaction without purification.

EXAMPLE 2

3-Nitrotrichlorovinylbenzene

To a solution of 17.02 grams (0.426 mol) of sodium hydroxide in 300 ml of methanol in a 2 liter, 3-neck flask equipped with a mechanical stirrer, a thermometer and a dropping funnel was added 106.19 grams (0.37 mol) of crude 3-nitrotetrachloroethylbenzene from the previous reaction in 140 ml of methanol. The temperature of the reaction mixture rose from 25° to 31° C. and a large amount of white solid (sodium chloride and the product) precipitated during the 1 hour addition period. The addition funnel was rinsed with an additional 10 ml of methanol at the end of the addition. The reaction mixture was stirred for 1.25 hours and then 4.7 ml of concentrated hydrochloric acid was added dropwise to neutralize the excess base. This mixture was used directly in the subsequent hydrogenation.

Crystalline 3-nitrotrichlorovinylbenzene can be isolated at this point by filtration and the sodium chloride can be removed by washing the cake with water. The solid and the methanol filtrate were thus combined and hydrogenated with good results.

EXAMPLE 3

3-Trichlorovinylaniline Hydrochloride

The slurry of 92 grams (0.37 mol) of crude 3-nitrotrichlorovinylbenzene in methanol was transferred to a 2-liter glass-lined vessel with 350 ml of additional methanol and 80 ml of concentrated hydrochloric acid was added. To this slurry was charged 0.46 grams of 5% palladium-on-carbon and the mixture was shaken under 40 psig hydrogen pressure at ambient temperature on the Parr apparatus.

After approximately 24 hours the theoretical amount of hydrogen had been consumed. The reaction mixture was degassed with nitrogen and filtered through 20 grams of Super-cel. The filter cake was rinsed with 150 ml of methanol and 400 ml of water was added to the combined filtrates. The methanol was removed in vacuo. The resulting slurry of aniline hydrochloride in water (pH 2) was stirred with cooling in an ice-water bath for 1 hour and then filtered. The filter cake was washed with 85 ml of cold water and the solid was dried for 16 hours at 60° C. under house vacuum to give 86.82 grams (91.3%) of 3-trichlorovinylaniline hydrochloride. Melting point 248° C. (with decomposition). Basification and extractive workup of the filtrate gave 3.86 grams of material which contained 67% of 3-trichlorovinylaniline by gas chromatographic analysis and thus represented 3% of the theoretical yield.

EXAMPLE 4

The procedure in Example 3 was repeated with 0.92 g of 5% palladium on carbon as the catalyst. The hydrogenation was completed in 6.5 hours. A 91% yield of 3-trichlorovinylaniline hydrochloride was obtained.

EXAMPLE 5

The procedure in Example 3 was repeated at 80 psig hydrogen pressure. There was an exotherm during the hydrogenation and it was completed in 7 hours. A 90% yield of 3-trichlorovinylaniline hydrochloride was obtained.

What is claimed is:

1. A process for preparing 3-trichlorovinyl aniline and acid addition salts thereof which comprises hydrogenating in an alcoholic acidic medium 3-trichlorovinylnitrobenzene under an atmosphere of hydrogen at from 15 to 105 psig in the presence of from 0.2 to 2.0% supported palladium catalyst containing from 5 to 10% palladium on a substrate.

2. The process of claim 1 wherein the palladium is supported on a substrate of carbon.

3. The process of claim 1 wherein the hydrogenation is initiated at a pressure of from 30-50 psig.

4. The process of claim 3 wherein the hydrogenation is initiated at a pressure of about 40 psig.

5. The process of claim 1 wherein the pH of the reaction mixture is about 2.

6. The process of claim 1 wherein the medium is acidic by the presence of hydrochloric or sulfuric acids.

7. The process of claim 6 wherein the medium is acidic by the presence of anhydrous hydrogen chloride or concentrated aqueous hydrochloric acid.

8. The process of claim 1 wherein the reaction is carried out in a solvent or methanol or ethanol optionally also containing benzene or tolune or methylene chloride.

9. The process of claim 8 wherein the reaction is carried out in a solvent of methanol or ethanol.

* * * * *